(12) United States Patent
Wells et al.

(10) Patent No.: US 9,452,200 B2
(45) Date of Patent: *Sep. 27, 2016

(54) ACTIVATORS OF CXCR3 FOR THE TREATMENT OF ANGIOPATHIES OF THE EYE

(71) Applicant: University of Pittsburgh—Of the Commonwealth System of Higher Education, Pittsburgh, PA (US)

(72) Inventors: Alan H. Wells, Pittsburgh, PA (US); Cecelia C. Yates-Binder, Pittsburgh, PA (US); Joel S. Schuman, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/878,370

(22) Filed: Oct. 8, 2015

(65) Prior Publication Data

US 2016/0022779 A1 Jan. 28, 2016

Related U.S. Application Data

(63) Continuation of application No. 14/240,132, filed as application No. PCT/US2012/052049 on Aug. 23, 2012, now Pat. No. 9,180,167.

(60) Provisional application No. 61/527,872, filed on Aug. 26, 2011.

(51) Int. Cl.
| | |
|---|---|
| *A61K 38/16* | (2006.01) |
| *C07K 14/00* | (2006.01) |
| *A61P 43/00* | (2006.01) |
| *A61K 38/21* | (2006.01) |
| *A61K 38/19* | (2006.01) |
| *A61K 47/48* | (2006.01) |
| *A61K 9/00* | (2006.01) |

(52) U.S. Cl.
CPC ........... *A61K 38/217* (2013.01); *A61K 38/195* (2013.01); *A61K 47/4823* (2013.01); *A61K 47/48215* (2013.01); *A61K 9/0048* (2013.01)

(58) Field of Classification Search
CPC ............. A61K 38/195; A61K 9/0048; A61K 47/4823; A61K 47/48215; A61K 38/217
See application file for complete search history.

(56) References Cited

U.S. PATENT DOCUMENTS

| | | |
|---|---|---|
| 5,994,292 A | 11/1999 | Tosato et al. |
| 2007/0087001 A1 | 4/2007 | Taylor et al. |
| 2013/0053319 A1 | 2/2013 | Yates-Binder et al. |

FOREIGN PATENT DOCUMENTS

| | | |
|---|---|---|
| EP | 2 287 183 | 2/2011 |
| WO | WO 2005/113597 | 12/2005 |
| WO | WO 2007/033215 | 3/2007 |
| WO | WO 2007/149542 | 12/2007 |

OTHER PUBLICATIONS

Addison et al., "The CXC Chemokine Receptor 2, CXCR2, Is the Putative Receptor for ELR+ CXC Chemokine-Induced Angiogenic Activity," *J. Immunol.*, 165:5269-5277, 2000.
Berendsen, "A Glimpse of the Holy Grail?" *Science*, vol. 282:642-643, 1998.
Bodnar et al., "IP-10 Blocks Vascular Endothelial Growth Factor-Induced Endothelial Cell Motility and Tube Formation via Inhibition of Calpain," *Circ Res* 98:617-625, 2006.
Bodnar et al., "IP-10 induces dissociation of newly formed blood vessels," *J Cell Sci.*, 122:2064-2077, 2009.
Bradley et al., "Limits of Cooperativity in a Structurally Modular Protein: Response of the Notch Ankyrin Domain to Analogous Alanine Substitutions in Each Repeat," *J. Mol. Biol.*, vol. 324:373-386, 2002.
Campanella et al., "CXCR3 and Heparin Binding Sites of the Chemokine IP-10 (CXCL10)," *J. Biol. Chem.*, vol. 278:17066-17074, 2003.
Ingrams, et al., "Sinus Surgery: Does Mitomycin C Reduce Stenosis?" *Laryngoscope*, vol. 108:883-886, 1998.
Lee et al., "Intravitreal Bevacizumab (Avastin) Treatment of Neovascular Glaucoma in Ocular Ischemic Syndrome," *Korean J. Opthalmol.*, vol. 23:132-134, 2009.
Mabeta et al., "A Comparative Study on the Anti-Angiogenic Effects of DNA-Damaging and Cytoskeletal-Disrupting Agents," *Angiogenesis*, vol. 12:81-90, 2009.
Mehvar, "Dextrans for Targeted and Sustained Delivery of Therapeutic and Imaging Agents," *J. Control. Rel.*, vol. 69:1-25, 2000.
Ngo et al., "Computational Complexity, Protein Structure Prediction, and the Levinthal Paradox," The Protein Folding Problem and Tertiary Structure Prediction, pp. 491-494, 1994.
Rudinger, "Characteristics of the Amino Acids as Components of a Peptide Hormone Sequence," *Peptide Hormones*, University Park Press, Baltimore, pp. 1-7, 1976.
Sigma Genosys, "Designing Custom Peptides," www.sigma-genosys.com/peptide_design.asp, downloaded Dec. 16, 2004, 2 pages.
Stroke et al., "Identification of CXCR3 Receptor Agonists in Combinatorial Small-Molecule Libraries," *Biochem. Biophys. Res. Comm.*, vol. 349:221-228, 2006.
Voet, "Hemoglobin: Protein Function in Microcosm", *Biochemistry*, Second Ed., John Wiley & Sons, Inc., New York, pp. 235-241, 1995.
Yates-Binder et al., "An IP-10 (CXCL10)-Derived Peptide Inhibits Angiogenesis," *PLoS ONE* 7:e40812, 2012.

*Primary Examiner* — Julie Ha
*Assistant Examiner* — Li Ni Komatsu
(74) *Attorney, Agent, or Firm* — Klarquist Sparkman, LLP

(57) ABSTRACT

The present disclosure describes methods of treating angiogenic disorders of the eye, such as macular degeneration, restenosis following glaucoma treatment or diabetic retinopathy, by administering an activator of C-X-C chemokine receptor 3 (CXCR3). In some embodiments, the activator of CXCR3 is interferon-γ-inducible 10 kDa protein (IP-10) or a fragment or variant thereof, such as a fragment comprising or consisting of the C-terminal α-helix of IP-10. In other embodiments, the activator of CXCR3 is platelet factor 4 (PF4) or a fragment or variant thereof.

26 Claims, No Drawings

SEQUENCE LISTING

<160> NUMBER OF SEQ ID NOS: 11

<210> SEQ ID NO 1
<211> LENGTH: 98
<212> TYPE: PRT
<213> ORGANISM: Homo sapiens

<400> SEQUENCE: 1

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 2
<211> LENGTH: 21
<212> TYPE: PRT
<213> ORGANISM: Homo sapiens

<400> SEQUENCE: 2

Glu Ser Lys Ala Ile Lys Asn Leu Leu Lys Ala Val Ser Lys Glu Arg
1               5                   10                  15

Ser Lys Arg Ser Pro
            20

<210> SEQ ID NO 3
<211> LENGTH: 70
<212> TYPE: PRT
<213> ORGANISM: Homo sapiens

<400> SEQUENCE: 3

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70

<210> SEQ ID NO 4
<211> LENGTH: 29
<212> TYPE: PRT
<213> ORGANISM: Homo sapiens

<400> SEQUENCE: 4

Asp Leu Gln Cys Leu Cys Val Lys Thr Thr Ser Gln Val Arg Pro Arg
1               5                   10                  15

His Ile Thr Ser Leu Glu Val Ile Lys Ala Gly Pro His

```
                    20                  25

<210> SEQ ID NO 5
<211> LENGTH: 22
<212> TYPE: PRT
<213> ORGANISM: Homo sapiens

<400> SEQUENCE: 5

Pro Glu Ser Lys Ala Ile Lys Asn Leu Leu Lys Ala Val Ser Lys Glu
1               5                   10                  15

Arg Ser Lys Arg Ser Pro
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 6

Glu Ser Lys Ala Ile Lys Asn Leu Leu Lys Ala Val Ser Lys Glu Met
1               5                   10                  15

Ser Lys Arg Ser Pro
            20

<210> SEQ ID NO 7
<211> LENGTH: 98
<212> TYPE: PRT
<213> ORGANISM: Mus musculus

<400> SEQUENCE: 7

Met Asn Pro Ser Ala Ala Val Ile Phe Cys Leu Ile Leu Leu Gly Leu
1               5                   10                  15

Ser Gly Thr Gln Gly Ile Pro Leu Ala Arg Thr Val Arg Cys Asn Cys
            20                  25                  30

Ile His Ile Asp Asp Gly Pro Val Arg Met Arg Ala Ile Gly Lys Leu
        35                  40                  45

Glu Ile Ile Pro Ala Ser Leu Ser Cys Pro Arg Val Glu Ile Ile Ala
    50                  55                  60

Thr Met Lys Lys Asn Asp Glu Gln Arg Cys Leu Asn Pro Glu Ser Lys
65                  70                  75                  80

Thr Ile Lys Asn Leu Met Lys Ala Phe Ser Gln Lys Arg Ser Lys Arg
                85                  90                  95

Ala Pro

<210> SEQ ID NO 8
<211> LENGTH: 21
<212> TYPE: PRT
<213> ORGANISM: Mus musculus

<400> SEQUENCE: 8

Glu Ser Lys Thr Ile Lys Asn Leu Met Lys Ala Phe Ser Gln Lys Arg
1               5                   10                  15

Ser Lys Arg Ala Pro
            20

<210> SEQ ID NO 9
<211> LENGTH: 22
<212> TYPE: PRT
<213> ORGANISM: Mus musculus
```

```
<400> SEQUENCE: 9

Pro Glu Ser Lys Thr Ile Lys Asn Leu Met Lys Ala Phe Ser Gln Lys
1               5                   10                  15

Arg Ser Lys Arg Ala Pro
            20

<210> SEQ ID NO 10
<211> LENGTH: 13
<212> TYPE: PRT
<213> ORGANISM: Homo sapiens

<400> SEQUENCE: 10

Pro Leu Tyr Lys Lys Ile Ile Lys Lys Leu Leu Glu Ser
1               5                   10

<210> SEQ ID NO 11
<211> LENGTH: 18
<212> TYPE: PRT
<213> ORGANISM: Homo sapiens

<400> SEQUENCE: 11

Leu Asp Leu Gln Ala Pro Leu Tyr Lys Lys Ile Ile Lys Lys Leu Leu
1               5                   10                  15

Glu Ser
```

ACTIVATORS OF CXCR3 FOR THE TREATMENT OF ANGIOPATHIES OF THE EYE

CROSS REFERENCE TO RELATED APPLICATIONS

This is a continuation of U.S. application Ser. No. 14/240,132, filed Feb. 21, 2014, issued as U.S. Pat. No. 9,180,167 on Nov. 10, 2015, which is the U.S. National Stage of International Application No. PCT/US2012/052049, filed Aug. 23, 2012, published in English under PCT Article 21(2), which claims the benefit of U.S. Provisional Application No. 61/527,872, filed Aug. 26, 2011. All of the above-referenced application are herein incorporated by reference in their entirety.

ACKNOWLEDGMENT OF GOVERNMENT SUPPORT

This invention was made with government support under grant number GM 069668 awarded by the National Institutes of Health. The government has certain rights in the invention.

FIELD

This disclosure concerns methods for treating angiogenic disorders of the eye, particularly methods that include administration of a CXCR3 activator.

BACKGROUND

The formation of new blood vessels, whether by angiogenesis or vasculogenesis, is critical for several physiological processes including embryogenesis, organogenesis and vascular remodeling. Angiogenesis is regulated by a complex and interrelated system of pathways that involve various angiogenic and angiostatic factors (Strieter et al., *Eur J Cancer* 42:768-778, 2006; Dimberg, *Curr Top Microbiol Immunol* 341:59-80, 2010). Over- or under-expression of angiogenic or angiostatic factors results in pathologic conditions, as noted for excessive angiogenesis in tumors, or untimely termination of angiogenesis that results in unhealed chronic wounds (Balestrieri et al., *Cardiovasc Res* 78:250-256, 2008). Researchers have sought to better understand the signaling pathways of these angiogenesis regulators to provide new therapies to modulate these and other pathological conditions.

Recent evidence demonstrates that members of the CXC chemokine family can act as either angiogenic or angiostatic factors, depending on the presence of the ELR (Glu-Leu-Arg) motif in their amino terminus (Strieter et al., *J Biol Chem* 270:27348-57 1995). Among this small family of chemokines are CXC chemokines CXCL11 (IP-9/ITAC), CXCL10 (IP-10-interferon-γ-inducible 10 kDa protein), and CXCL9 (Mig); all of these lack the canonical N-terminal ELR sequence (Godessart and Kunkel, *Curr Opin Immunol* 6:670-675, 2001) and bind the ubiquitous CXCR3 chemokine receptor. CXCR3 has two isoforms (CXCR3-A and CXCR3-B) that regulate chemotaxis and proliferation in various cells types (Kelsen et al., *Am J Physiol Lung Cell Mol Physiol* 287:L584-591, 2004), acting as an angiostatic agent in endothelial cells (Lasagni et al., *J Exp Med* 197:1537-1549, 2003; Bodnar et al., *Circ Res* 98:617-625, 2006). All of the CXCR3-binding chemokines (CXCL4/PF4, CXCL9/Mig, CXCL10/IP-10 and CXCL11/IP-9/I-TAC) have been reported to be angiostatic and have antitumor activity via signaling through CXCR3; resulting in inhibition of VEGF and bFGF induced angiogenesis and eventual in vitro and in vivo regression of nascent vessels (Addison et al., *J Immunol* 165:5269-5277, 2000; Bodnar et al., *Circ Res* 98:617-625, 2006; Bodnar et al., *J Cell Sci* 122:2064-2077, 2009; Yates-Binder et al., *PLoS ONE* 7(7):e40812, 2012).

SUMMARY

Provided herein are methods of treating angiogenic disorders of the eye. In some embodiments, the method includes selecting a subject with an angiogenic disorder of the eye, and administering to the subject a therapeutically effective amount of an activator of CXCR3. Also provided are methods of treating or inhibiting aberrant angiogenesis of the eye. In some embodiments, the method includes selecting a subject with aberrant angiogenesis of the eye, and administering to the subject a therapeutically effective amount of an activator of CXCR3.

In some embodiments of the disclosed methods, the CXCR3 activator is an IP-10 protein or biologically active peptide fragment or variant thereof. In other embodiments, the CXCR3 activator is a PF4 protein or biologically active peptide fragment or variant thereof. In some examples, the protein or peptide is modified to prevent the protein or peptide from crossing the blood-brain or blood barriers.

The foregoing and other objects and features of the disclosure will become more apparent from the following detailed description.

SEQUENCE LISTING

The amino acid sequences listed in the accompanying sequence listing are shown using standard three letter code for amino acids, as defined in 37 C.F.R. 1.822. The Sequence Listing is submitted as an ASCII text file, created on Sep. 24, 2015, 4.83 KB, which is incorporated by reference herein. In the accompanying sequence listing:

SEQ ID NO: 1 is the amino acid sequence of human IP-10.
SEQ ID NO: 2 is the amino acid sequence of a human IP-10 fragment.
SEQ ID NO: 3 is the amino acid sequence of human PF4.
SEQ ID NO: 4 is the amino acid sequence of a human PF4 fragment.
SEQ ID NO: 5 is the amino acid sequence of a human IP-10 fragment.
SEQ ID NO: 6 is the amino acid sequence of a human IP-10 peptide variant.
SEQ ID NO: 7 is the amino acid sequence of mouse IP-10.
SEQ ID NO: 8 is the amino acid sequence of a mouse IP-10 fragment.
SEQ ID NO: 9 is the amino acid sequence of a mouse IP-10 fragment.
SEQ ID NO: 10 is the amino acid sequence of a human PF4 fragment.
SEQ ID NO: 11 is the amino acid sequence of a human PF4 fragment.

DETAILED DESCRIPTION

I. Abbreviations
 AMD age-related macular degeneration
 CXCL C-X-C chemokine ligand
 CXCR C-X-C chemokine receptor IP-10 interferon-γ-inducible 10 kDa protein
IM intramuscular
IOP intraocular pressure
IV intravenous
PEG polyethylene glycol
PF4 platelet factor 4
VEGF vascular endothelial growth factor
WMD wet macular degeneration II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Activator of CXCR3: Refers to any type of compound, such as a protein, peptide, small molecule, nucleic acid molecule, organic compound or inorganic compound that promotes or enhances one or more functions or activities of CXCR3. In some embodiments, the CXCR3 activator is a protein ligand that binds CXCR3. In some examples, the CXCR3 activator is IP-10 or a biologically active fragment or variant thereof (such as a fragment or variant capable of inhibiting angiogenesis). In other examples, the CXCR3 activator is PF4 or a biologically active fragment or variant thereof. In yet other examples, the activator is a CXCR3-specific antibody that activates CXCR3.

Administration: The introduction of a composition (such as a protein or peptide) into a subject by a chosen route. For example, if the chosen route is intravenous, the composition is administered by introducing the composition into a vein of the subject. Exemplary routes of administration include, but are not limited to, injection (such as intraocular, subcutaneous, intramuscular, intradermal, intraperitoneal, and intravenous), oral, intraductal, sublingual, transdermal, intranasal, topical, inhalation routes and via a medical implant.

Angiogenesis: The physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one, and a number of other disorders result from aberrant angiogenesis. "Aberrant angiogenesis" refers to uncontrolled or pathologic angiogenesis present in a number of different diseases, including disorders of the eye, for example, restenosis following glaucoma treatment, wet macular degeneration, diabetic retinopathy, retinopathy of prematurity or neovascular glaucoma.

Angiogenic disorder: Any condition, disease or disorder resulting from aberrant angiogenesis. Examples of angiogenic disorders include, for example, cancer, diabetic retinopathy, macular degeneration, retinopathy of prematurity, corneal neovascularization and neovascular glaucoma. This term also includes conditions resulting from aberrant pathologic angiogenesis resulting from medical interventions, such as restenosis following glaucoma treatment and angiogenesis resulting from corneal transplant.

Angiogenic disorder of the eye: Includes any intraocular or external angiogenic disorder of the eye. For example, intraocular angiogenic disorders include disorders inside the eye such as diabetic retinopathy, wet macular degeneration, retinopathy of prematurity, restenosis following glaucoma treatment and neovascular glaucoma. External angiogenic disorders of the eye are exterior to the eye, for example corneal neovascularization.

Biologically active fragment or variant: Biologically active fragments (also referred to as biologically active peptides) or variants include any fragments or variants of a protein that retain an activity of the protein. In the context of the present disclosure, a biologically active fragment or variant of a protein (such as IP-10 or PF4) that binds CXCR3 is one that retains the ability to bind CXCR3 and/or retains the ability to inhibit angiogenesis. In some embodiments, the peptide variant comprises no more than 1, no more than 2, nor more than 3, no more than 4 or no more than 5 amino acid substitutions; such substitutions can be conservative or non-conservative substitutions.

Blood-brain barrier: A separation of circulating blood and the brain extracellular fluid in the central nervous system. It occurs along all capillaries and consists of tight junctions around the capillaries that do not exist in normal circulation. Endothelial cells restrict the diffusion of microscopic objects (e.g. bacteria) and large or hydrophilic molecules into the cerebrospinal fluid, while allowing the diffusion of small hydrophobic molecules ($O_2$, hormones, $CO_2$). Cells of the barrier actively transport metabolic products such as glucose across the barrier with specific proteins. The eye spaces (the vitreous and aqueous humors) are considered on the CNS side of the barrier.

Conservative variants: "Conservative" amino acid substitutions are those substitutions that do not substantially affect or decrease an activity or antigenicity of a protein, such as IP-10 or an IP-10 peptide, or PF4 or a PF4 peptide. For example, IP-10 or PF4 (or a fragment thereof, such as any one of SEQ ID NOs: 2, 4-6 and 8-11) can include at most about 1, at most about 2, at most about 5, and most about 10, or at most about 15 conservative substitutions (such as 1, 2, 3, 4, 5, 6, 7, 8, 9, 10, 11, 12, 13, 14 or 15 conservative substitutions, such as 1 to 3, 1 to 5, 1 to 10, or 2 to 4 conservative substitutions, and retain biological activity, such as the ability to bind CXCR3 and/or inhibit angiogenesis. In particular examples, IP-10 peptide variants and PF4 peptide variants have no more than 3 conservative amino acid substitutions. Specific, non-limiting examples of a conservative substitution include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variant also includes the use of a substituted amino acid in place of an unsubstituted parent amino acid. Non-conservative substitutions are those that reduce an activity or antigenicity.

Corneal neovascularization: Excessive ingrowth of blood vessels from the limbal vascular plexus into the cornea, caused by a low reception of oxygen. One of the most common causes is from wearing contact lenses, particular extended wear contact lenses. Corneal neovascularization is also a common response to injury of the eye and can also occur after corneal transplant.

CXCR3 (C-X-C chemokine receptor 3): A G protein-coupled receptor with selectivity for four chemokines, termed CXCL4/PF4 (platelet factor 4), CXCL9/Mig (monokine induced by interferon-γ), CXCL10/IP-10 (interferon-γ-inducible 10 kDa protein) and CXCL11/I-TAC (interferon-inducible T cell a-chemoattractant). Binding of chemokines to this protein induces cellular responses that are involved in leukocyte traffic, most notably integrin activation, cytoskeletal changes and chemotactic migration. Alternatively spliced transcript variants encoding different isoforms have been found for this gene. One of the isoforms (CXCR3-B) shows high affinity binding to chemokine CXCL4/PF4.

Dextran: A complex, branched glucan (polysaccharide made of many glucose molecules) composed of chains of varying lengths (from 3 to 2000 kilodaltons).

Diabetic retinopathy: A disorder in which damage to the retina occurs due to complications of diabetes mellitus. Proliferative retinopathy, which generally occurs at advanced stages of the disease, is characterized by abnormal formation of new blood vessels on the vitreous surface, extending into the vitreous cavity.

Glaucoma: An eye disorder in which the optic nerve suffers damage, permanently damaging vision in the affected eye(s) and progressing to complete blindness if untreated. It is generally associated with increased pressure of the fluid in the eye (aqueous humor).

IP-10 (interferon-γ-inducible 10 kDa protein): A chemokine of the CXC subfamily and ligand for the receptor CXCR3. Binding of this protein to CXCR3 results in pleiotropic effects, including stimulation of monocytes, natural killer and T-cell migration, modulation of adhesion molecule expression, and inhibition of vessel formation. IP-10 is also known as chemokine (C-X-C motif) ligand 10 (CXCL10). IP-10 sequences are publically available, such as through GenBank (see, for example, Gene ID 3627 for human IP-10 sequences; see also GenBank Accession No. P02778). Exemplary human and mouse IP-10 sequences are set forth herein as SEQ ID NO: 1 and SEQ ID NO: 7, respectively. Exemplary IP-10 peptide fragments and variants are set forth herein as SEQ ID NOs: 2, 5, 6, 8 and 9.

Macular degeneration: A condition resulting in atrophy or degeneration of the macula. Age-related macular degeneration is a leading cause of visual loss in the elderly. There are two different forms of macular degeneration, referred to as the dry and wet forms. In atrophic macular degeneration (the dry form), there is pigmentary disturbance in the macular region but no elevated macular scar and no hemorrhage or exudation in the region of the macula. In contrast, in exudative macular degeneration (the wet form), there is formation of a subretinal network of choroidal neovascularization.

Neovascular glaucoma: A type of glaucoma that is very difficult to treat. This condition is often caused by proliferative diabetic retinopathy or central retinal vein occlusion. Neovascular glaucoma may also be triggered by other conditions that result in ischemia of the retina or ciliary body. Individuals with poor blood flow to the eye are highly at risk for this condition. Neovascular glaucoma results when new, abnormal vessels begin developing in the angle of the eye that begin blocking the drainage. Patients with this condition begin to rapidly lose their eyesight. Sometimes, the disease appears very rapidly, especially after cataract surgery.

Peptide or polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide," "peptide," or "protein" as used herein are intended to encompass any amino acid sequence and include modified sequences such as glycoproteins. The terms "polypeptide" and "peptide" are specifically intended to cover naturally occurring proteins, as well as those which are recombinantly or synthetically produced.

In some embodiments, a polypeptide is between 10 and 600 amino acids in length, including 10 to 100, 10 to 50, or 10 to 30, amino acids in length. In particular examples, a CXCR3 activator is a IP-10 peptide of about 19 to about 23 amino acids, such as about 21 or 22 amino acids. In other specific examples, the CXCR3 activator is a PF4 peptide of about 27 to about 31 amino acids, such as about 29 amino acids. In other examples, the PF4 peptide is about 10 to about 20 amino acids, such as about 13 to about 18 amino acids, for example 13 amino acids or 18 amino acids.

An "IP-10 polypeptide" or "IP-10 peptide" is a series of contiguous amino acid residues from an IP-10 protein. Similarly, a "PF4 polypeptide" or "PF4 peptide" is a series of contiguous amino acid residues from an IP-10 protein. In some examples, the term further refers to variations of these peptides in which there are conservative substitutions of amino acids, so long as the variations do not alter by more than about 20% (such as no more than about 1%, about 5%, or about 10%) the ability of the peptide to inhibit angiogenesis.

A "residue" refers to an amino acid or amino acid mimetic incorporated in a polypeptide by an amide bond or amide bond mimetic.

PF4 (platelet factor 4): A small cytokine belonging to the CXC chemokine family. PF4 is a 70-amino acid protein that is released from the alpha-granules of activated platelets and binds with high affinity to heparin. Its major physiologic role appears to be neutralization of heparin-like molecules on the endothelial surface of blood vessels, thereby inhibiting local antithrombin III activity and promoting coagulation. As a strong chemoattractant for neutrophils and fibroblasts, PF4 is believed to play a role in inflammation and wound repair. PF4 is also known as CXCL4. PF4 is known to bind the B isoform of CXCR3 (CXCR3-B). Sequences for PF4 are publically available (see, for example, GenBank Gene ID 5196). An exemplary human PF4 sequence is set forth herein as SEQ ID NO: 3. Exemplary PF4 peptide sequences are set forth herein as SEQ ID NOs: 4, 10 and 11.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. For topical application to the eye, agents can be mixed, for example, with artificial tears and other emulsions.

Polyethylene glycol (PEG): A polyether compound with many applications from industrial manufacturing to medicine. PEG has also been known as polyethylene oxide (PEO) or polyoxyethylene (POE), depending on its molecular weight, and under the tradename Carbowax. PEG, PEO, or POE refers to an oligomer or polymer of ethylene oxide. The three names are chemically synonymous, but historically PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol.

Restenosis: The reoccurrence of stenosis, the narrowing of a blood vessel, leading to restricted blood flow. Stenosis (or restenosis) is a form of response to injury leading to wall thickening, narrowing of the lumen, and loss of function in the tissue supplied by the particular passageway. Physical injury during an interventional procedure (such as glaucoma surgery) results in damage to epithelial lining of the tube. The repair of tissues following a physical injury involves regeneration (the replacement of injured cells by cells of the same type) and fibrosis (the replacement of injured cells by connective tissue). The process of fibrosis includes, among other events, the formation of new blood vessels (angiogenesis).

Retinopathy of prematurity: An eye disease that affects prematurely born babies. It is thought to be caused by disorganized growth of retinal blood vessels which may result in scarring and retinal detachment. The disease can be mild and may resolve spontaneously, but it may lead to blindness in serious cases.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a particular polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. In addition, Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, 90%, 95%, 96%, 97%, 98% or 99% sequence identity counted over the full length alignment with the amino acid sequence of the polypeptide using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Living multi-cellular vertebrate organisms, a category that includes both human and veterinary subjects, including human and non-human mammals. In one example, a subject is one who has an angiopathy of one or both eyes.

Therapeutically effective amount: A quantity of a specified agent (such as a CXCR3 activator) sufficient to achieve a desired effect in a subject, cell or culture being treated with that agent. In some embodiments, a therapeutically effective amount of a CXCR3 activator is an amount of CXCR3 activator that prevents or inhibits angiogenesis of the eye (such as intraocular angiogenesis or external angiogenesis), such as pathological angiogenesis that occurs in connection with an angiopathy of the eye. In some embodiments, a therapeutically effective amount of a CXCR3 activator is an amount sufficient to prevent or ameliorate one or more symptoms of an angiogenic disorder in a subject.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety; sequences associated with the disclosed GenBank numbers and GenBank Gene ID numbers are incorporated by reference for the sequence available on Aug. 26, 2011. In case of conflict, the present specification, including explanations of terms, will control. In addition, the materials, methods, and examples are illustrative only and not intended to be limiting.

III. Overview of Several Embodiments

Provided herein are methods of treating an angiogenic disorder of the eye. In some embodiments, the method includes selecting a subject with an angiogenic disorder of the eye, and administering to the subject a therapeutically effective amount of an activator of CXCR3. In some examples, the subject selected is one having an angiogenic disorder in one or both eyes. Angiogenic disorders of the eye include both intraocular angiogenic disorders and external angiogenic disorders of the eye. Intraocular disorders include any diseases or disorders inside the eye, such as a subject having restenosis following glaucoma treatment, wet macular degeneration, diabetic retinopathy, retinopathy of prematurity or neovascular glaucoma. External angiogenic disorders of the eye include disorders external to the eye, such as corneal neovascularization.

Also provided is a method of treating or inhibiting aberrant angiogenesis of the eye. In some embodiments, the method includes selecting a subject with aberrant angiogenesis of the eye, and administering to the subject a therapeutically effective amount of an activator of CXCR3. In some examples, the subject selected is one exhibiting aberrant angiogenesis in one or both eyes.

In some embodiments of the disclosed methods, the angiogenic disorder is, or the aberrant angiogenesis caused by, restenosis following glaucoma treatment, wet macular degeneration, diabetic retinopathy, retinopathy of prematurity, neovascular glaucoma or corneal neovascularization. However, any disorder of the eye with a pathologic angiogenic component is contemplated for treatment with the disclosed methods.

In some embodiments, the activator of CXCR3 comprises a protein that binds CXCR3. In some embodiments, the protein that binds CXCR3 comprises IP-10, or a biologically active fragment or variant thereof, such as an IP-10 peptide. In some embodiments, the IP-10 is human IP-10 of SEQ ID NO: 1 or mouse IP-10 of SEQ ID NO: 7. In some examples, the IP-10 protein is at least 80%, at least 85%, at least 90%, at least 95%, at least 96%, at least 97%, at least 98% or at least 99% identical to SEQ ID NO: 1 or SEQ ID NO: 7. In specific non-limiting examples, the amino acid sequence of the IP-10 protein comprises or consists of SEQ ID NO: 1 or SEQ ID NO: 7. In other embodiments, the protein that binds CXCR3 is PF4 (such as human PF4), or a biologically active fragment or variant thereof, such as a PF4 peptide. In some examples, the PF4 protein is at least 80%, at least 85%, at least 90%, at least 95%, at least 96%, at least 97%, at least 98% or at least 99% identical to SEQ ID NO: 3. In specific non-limiting examples, the amino acid sequence of the PF4 protein comprises or consists of SEQ ID NO: 3.

The biologically active fragment or variant of IP-10 or PF4 can be any fragment or variant that retains the capacity to inhibit angiogenesis. In some embodiments, the biologically active fragment of IP-10 is a fragment comprising or consisting of amino acid residues 77-98 or residues 78-98 of SEQ ID NO: 1. In some examples, the biologically active fragment of IP-10 comprises an amino acid sequence at least 80%, at least 85%, at least 90%, at least 95%, at least 96%, at least 97%, at least 98% or at least 99% identical to SEQ ID NO: 2, SEQ ID NO: 5, SEQ ID NO: 6, SEQ ID NO: 8 or SEQ ID NO: 9. In some examples, the biologically active fragment of IP-10 comprises an amino acid sequence at least 80%, at least 90%, at least 95%, at least 96%, at least 97%, at least 98% or at least 99% identical to SEQ ID NO: 2, SEQ ID NO: 5, SEQ ID NO: 6, SEQ ID NO: 8 or SEQ ID NO: 9, wherein the fragment is no more than 40 amino acids, such as a fragment 15 to 40, 20 to 40, 20 to 30, 20 to 25, or 21 to 23 amino acids in length. In some examples, the biologically active fragment of IP-10 consists of SEQ ID NO: 2, SEQ ID NO: 5, SEQ ID NO: 6, SEQ ID NO: 8 or SEQ ID NO: 9 and includes no more than 10 conservative amino acid substitutions, such as 1 to 10 or 1 to 5 or 1 to 3 conservative amino acid substitutions. In specific non-limiting examples, the amino acid sequence of the IP-10 fragment comprises or consists of SEQ ID NO: 2, SEQ ID NO: 5, SEQ ID NO: 6, SEQ ID NO: 8 or SEQ ID NO: 9.

In other embodiments, the biologically active fragment of PF4 is a fragment comprising or consisting of amino acid residues 7-35, residues 58-70 or residues 53-70 of SEQ ID NO: 3. In some examples, the biologically active fragment of PF4 comprises an amino acid sequence at least 80%, at least 85%, at least 90%, at least 95%, at least 96%, at least 97%, at least 98% or at least 99% identical to SEQ ID NO: 4, SEQ ID NO: 10 or SEQ ID NO: 11. In some examples, the biologically active fragment of PF4 comprises an amino acid sequence at least 80%, at least 90%, at least 95%, at least 96%, at least 97%, at least 98% or at least 99% identical to SEQ ID NO: 4, SEQ ID NO: 10 or SEQ ID NO: 11, wherein the fragment is no more than 40 amino acids, such as a fragment 15 to 40, 20 to 40, 25 to 35, 27 to 31, 28 to 30, or about 29 amino acids in length. In some examples, the biologically active fragment of PF4 consists of SEQ ID NO: 4, SEQ ID NO: 10 or SEQ ID NO: 11 and includes no more than 10 conservative amino acid substitutions, such as 1 to 10 or 1 to 5 or 1 to 3 conservative amino acid substitutions. In specific non-limiting examples, the amino acid sequence of the PF4 fragment comprises or consists of SEQ ID NO: 4, SEQ ID NO: 10 or SEQ ID NO: 11.

In some embodiments, the protein or peptide is modified to prevent the protein or peptide from crossing the blood-brain barrier when administered to the subject. The protein or peptide can be, for example, modified to increase hydrophobicity or to increase overall charge of the protein or peptide. In particular embodiments, modification comprises conjugation of the protein or peptide to a large inert molecule. In some examples, the modification comprises conjugation of the protein or peptide to polyethylene glycol (PEG) or dextran (see, for example, Mehvar, "Dextrans for targeted and sustained delivery of therapeutic and imaging agents," *J Control Release* 69(1):1-25, 2000).

The mode of administration of the protein or peptide will vary depending upon, for example, the disease or disorder to be treated and the stage or severity of the disease. In some embodiments, the protein or peptide is administered topically, by injection (such as by subconjunctival injection) or by medical implant.

In some examples, the protein or peptide is administered topically in a cream or eye drop to allow for adsorption into the eye.

In other examples, the protein or peptide is administered by injection into the vitreous humor or the aqueous humor.

The method can include a single injection of the protein or peptide, or multiple injections as needed, such as 2, 3, 4 or 5 injections.

In other examples, the protein or peptide is impregnated in the medical implant, is coated on the surface of the medical implant, or both.

The therapeutically effective amount of the agents administered can vary depending upon the desired effects and the subject to be treated. In one example, the method includes administration of at least 1 µg of a therapeutic agent to the subject (such as a human subject). For example, a human can be administered at least at least 0.01 µg, at least 0.1 µg, at least 1 µg or at least 1 mg of the agent as a single dose, or in multiple doses (such as daily doses), such as 10 µg to 100 µg per dose, 100 µg to 1000 µg per dose, for example 10 µg per dose, 100 µg per dose, or 1000 µg per dose. In some examples, the subject is administered at least 1 µg (such as 1-100 µg) intravenously of the protein or peptide (such as a composition that includes any one of SEQ ID NOs: 1-11 or a variant thereof). In one non-limiting example, a subject is administered about 10 µg of the CXCR3 activator (such as an IL-10 peptide or a PF4 peptide). In another non-limiting example, a subject is administered about 100 µg of the CXCR3 activator (such as an IL-10 peptide or a PF4 peptide).

The dosage can be administered in divided doses (such as 2, 3, or 4 divided doses per day or over multiple days), or in a single dosage daily. In particular examples, the subject is administered the therapeutic composition on a multiple daily dosing schedule, such as at least two consecutive days, 10 consecutive days, and so forth, for example for a period of weeks, months, or years. In one example, the subject is administered the therapeutic composition daily for a period of at least 30 days, such as at least 2 months, at least 4 months, at least 6 months, at least 12 months, at least 24 months, or at least 36 months. In another example, the subject is administered about 3, about 4, about 5, about 5 or about 7 doses per week. In one example, the subject is administered a dose on days 1, 2, 4 and 7.

The compositions, such as those that include an IP-10 or PF4 peptide, can further include one or more biologically active or inactive compounds (or both), such as other agents known in the art for reducing or treating one or more signs or symptoms associated with aberrant angiogenesis and conventional non-toxic pharmaceutically acceptable carriers, respectively. For example, additional therapeutic agents which enhance the therapeutic effect of the disclosed compositions are included.

IV. IP-10, PF4 and Biologically Active Fragments and Variants Thereof

In some embodiments, the present disclosure contemplates the use of an IP-10 protein, or a biologically active peptide fragment or variant thereof, as an activator of CXCR3 to inhibit aberrant angiogenesis. Sequences for IP-10 proteins from a variety of different species are known in the art and are publically accessible, such as through the GenBank database. For example, IP-10 sequences are known for at least the following species: human (see GenBank Gene ID 3627), mouse (Gene ID 15945), rat (Gene ID 24592), pig (Gene ID 494019), chimpanzee (Gene ID 461242), dog (Gene ID 478432), cow (Gene ID 615107), macaque (Gene ID 574243), horse (Gene ID 100050993) and sheep (Gene ID 44297).

In some embodiments of the methods disclosed herein, the IP-10 protein is human IP-10, or a biologically active fragment or variant thereof. Exemplary IP-10 protein and peptide sequences are provided below.

Human IP-10 (full-length; GenBank Accession No. P02778):

(SEQ ID NO: 1)
MNQTAILICCLIFLTLSGIQGVPLSRTVRCTCISISNQPVNPRSLEKLE

IIPASQFCPRVEIIATMKKKGEKRCLNPESKAIKNLLKAVSKERSKRSP

Human IP-10 fragments/variants:

(SEQ ID NO: 2)
ESKAIKNLLKAVSKERSKRSP (SEQ ID NO: 5)
PESKAIKNLLKAVSKERSKRSP (SEQ ID NO: 6)
ESKAIKNLLKAVSKEMSKRSP

Mouse IP-10 (full-length):

(SEQ ID NO: 7)
MNPSAAVIFCLILLGLSGTQGIPLARTVRCNCIHIDDGPVRMRAIGKLE

IIPASLSCPRVEIIATMKKNDEQRCLNPESKTIKNLMKAFSQKRSKRAP

Mouse IP-10 fragments:

(SEQ ID NO: 8)
ESKTIKNLMKAFSQKRSKRAP (SEQ ID NO: 9)
PESKTIKNLMKAFSQKRSKRAP

In some embodiments of the methods, the IP-10 protein is at least 85%, at least 90%, at least 95%, at least 96%, at least 97%, at least 98 or at least 99% identical to SEQ ID NO: 1 or SEQ ID NO: 7. In some embodiments, the IP-10 peptide is at least 85%, at least 90%, at least 95%, at least 96%, at least 97%, at least 98 or at least 99% identical to SEQ ID NO: 2, SEQ ID NO: 5, SEQ ID NO: 6, SEQ ID NO: 8 or SEQ ID NO: 9. In some examples, the IP-10 peptide is no more than 40 amino acids in length, such as a biologically active fragment of IP-10 that is 15 to 40, 20 to 40, 20 to 30, 20 to 25, or 21 to 23 amino acids in length.

In other embodiments, the present disclosure contemplates the use of a PF4 protein, or a biologically active peptide fragment thereof, as an activator of CXCR3 to inhibit aberrant angiogenesis. Sequences for PF4 proteins from a variety of different species are known in the art and are publically accessible, such as through the GenBank database. For example, PF4 sequences are known for at least the following species: human (see GenBank Gene ID 5196), mouse (Gene ID 56744), rat (Gene ID 360918), chimpanzee (Gene ID 740477), cow (Gene ID 507790) and macaque (Gene ID 703451).

In some embodiments of the methods disclosed herein, the PF4 protein is human PF4, or a biologically active fragment thereof. Exemplary PF4 protein and peptide sequences are provided below.

Human PF4 protein (full-length):

(SEQ ID NO: 3)
EAEEDGDLQCLCVKTTSQVRPRHITSLEVIKAGPHCPTAQLIATLKNGR

KICLDLQAPLYKKIIKKLLES

Human PF4 peptides:

(SEQ ID NO: 4)
DLQCLCVKTTSQVRPRHITSLEVIKAGPH (SEQ ID NO: 10)
PLYKKIIKKLLES (SEQ ID NO: 11)
LDLQAPLYKKIIKKLLES

In some embodiments of the methods, the PF4 protein is at least 85%, at least 90%, at least 95%, at least 96%, at least 97%, at least 98 or at least 99% identical to SEQ ID NO: 3. In some embodiments, the PF4 peptide is at least 85%, at least 90%, at least 95%, at least 96%, at least 97%, at least 98 or at least 99% identical to SEQ ID NO: 4, SEQ ID NO: 10 or SEQ ID NO: 11. In some examples, the PF4 peptide is no more than 40 amino acids in length, such as a biologically active fragment of PF4 that is 10 to 40, 10 to 30, 15 to 40, 20 to 40, 20 to 30, 25 to 35, 10 to 20, 13 to 18, or 27 to 31 amino acids in length.

V. Treatment of Angiopathies of the Eye

The present disclosure provides methods for the treatment of angiogenic disorders of the eye by administration of a CXCR3 activator, such as an IP-10 or PF4 protein, or biologically active fragment thereof. Exemplary disorders that can be treated include, for example, restenosis following glaucoma treatment, wet macular degeneration, diabetic retinopathy, retinopathy of prematurity and neovascular glaucoma. However, any eye disorder having an angiopathic component is contemplated herein.

A. Restenosis Following Glaucoma Treatment

The clinical function of numerous medical implants and devices is dependent upon the device being able to effectively maintain an anatomical, or surgically created, space or passageway. Unfortunately, many devices implanted in the body are subject to a "foreign body" response from the surrounding host tissues. In particular, injury to tubular anatomical structures (such as blood vessels, the gastrointestinal tract, the male and female reproductive tract, the urinary tract, sinuses, spinal nerve root canals, lacrimal ducts, Eustachian tubes, the auditory canal, and the respiratory tract) from surgery and/or injury created by the implantation of medical devices can lead to a well known clinical problem called "stenosis" (or narrowing). Stenosis occurs in response to trauma to the epithelial lining or the entire body tube during the procedure, including virtually any manipulation which attempts to relieve obstruction of the passageway, and is a major factor limiting the effectiveness of invasive treatments for a variety of diseases (U.S. Patent Application Publication No. 20070299043), such as glaucoma.

Stenosis (or "restenosis" if the problem recurs after an initially successful attempt to open a blocked passageway) is a form of response to injury leading to wall thickening, narrowing of the lumen, and loss of function in the tissue supplied by the particular passageway. Physical injury during an interventional procedure results in damage to epithelial lining of the tube and the smooth muscle cells (SMCs) that make up the wall. The damaged cells, particularly SMCs, release cytokines, which recruit inflammatory cells such as macrophages, lymphocytes and neutrophils into the area. The white blood cells in turn release a variety of additional cytokines, growth factors, and tissue degrading enzymes that influence the behavior of the constituent cells of the wall (primarily epithelial cells and SMCs). Stimulation of the SMCs induces them to migrate into the inner aspect of the body passageway (often called the "intima"), proliferate and secrete an extracellular matrix—effectively filling all or parts of the lumen with reactive, fibrous scar tissue. Collectively, this creates a thickening of the intimal layer (known in some tissues as "neointimal hyperplasia") that narrows the lumen of the passageway and can be significant enough to obstruct its lumen.

The repair of tissues following a mechanical or surgical intervention involves two distinct processes: (1) regeneration (the replacement of injured cells by cells of the same type) and (2) fibrosis (the replacement of injured cells by connective tissue). There are four general components to the process of fibrosis (or scarring) including: formation of new blood vessels (angiogenesis), migration and proliferation of connective tissue cells (such as fibroblasts or smooth muscle cells), deposition of extracellular matrix (ECM), and remodeling (maturation and organization of the fibrous tissue).

Medical interventions for the treatment of glaucoma can result in restenosis. Thus, in some embodiments of the present disclosure, provided is a method of treating restenosis (which includes an angiogenic component) following glaucoma treatment by administering a therapeutically effective amount of a CXCR3 activator. In particular examples, the CXCR3 activator is an IP-10 protein or a biologically active peptide of IP-10. In specific non-limiting examples, the CXCR3 activator is a peptide comprising or consisting of the amino acid sequence of SEQ ID NO: 2 or SEQ ID NO: 5 (C-terminal fragments of human IP-10 that include the α-helix), or SQ ID NO: 6 (a variant of SEQ ID NO: 2). In other examples, the CXCR3 activator is a PF4 protein or a biologically active peptide of PF4. In specific non-limiting examples, the CXCR3 activator is a peptide comprising or consisting of the amino acid sequence of SEQ ID NO: 4 (a 29 amino acid fragment of PF4), SEQ ID NO: 10 (a 13 amino acid fragment of PF4) SEQ ID NO: 11 (an 18 amino acid fragment of PF4).

In one aspect of the present disclosure, the CXCR3 activator can be delivered via medical implants or implantable medical devices. For example, an IP-10 or PF4 peptide can be coated on a medical implant or impregnated within a medical implant, or both. In other embodiments, the CXCR3 activator is administered by injection into the aqueous humor.

The present disclosure provides a method of treating restenosis following glaucoma treatment, such as by preventing or inhibiting the formation of new blood vessels and/or the development of fibrosis, which typically occur during the course of this disease. In some embodiments, a subject diagnosed with restenosis is administered a therapeutically effective amount of an activator of CXCR3, such as an IP-10 protein (such as the IP-10 protein of SEQ ID NO: 1) or a biologically active fragment or variant of IP-10 (such as the IP-10 peptide of SEQ ID NO: 2, SEQ ID NO: 5, SEQ ID NO: 6, SEQ ID NO: 8 or SEQ ID NO: 9). In other embodiments, the subject is administered a PF4 protein (such as a PF4 protein of SEQ ID NO: 3) or a biologically active fragment of PF4 (such as the PF4 peptide of SEQ ID NO: 4, SEQ ID NO: 10 or SEQ ID NO: 11). The activator of CXCR3 can be administered by any suitable route, such as by injection into the aqueous humor.

B. Age-Related Macular Degeneration

Macular degeneration is a condition in which the cells of the macula (the central part of the retina) degenerate, resulting in loss of central visual acuity. The most common form of macular degeneration is age-related macular degeneration (AMD). AMD is the most common cause of irreversible loss of central vision and legal blindness in the elderly. It causes progressive damage to the macula, resulting in gradual loss of central vision. There are two forms, atrophic and neovascular macular degeneration. In atrophic degeneration (dry form), the tissues of the macula thin as photoreceptor cells disappear. There is currently no treatment for atrophic degeneration, though dietary supplements may help slow progression. In neovascular macular degeneration (wet form), abnormal blood vessels develop under the macula. These vessels may leak fluid and blood under the retina and eventually a mound of scar tissue develops under the retina.

Central vision becomes washed out and loses detail, and straight lines may appear wavy. For neovascular macular degeneration there are some treatments currently available, including the use of medication injected directly into the eye (e.g., anti-VEGF therapy), laser therapy in combination with a targeting drug (e.g., photodynamic therapy) and brachytherapy. However, repeated treatments can cause complications leading to loss of vision.

The present disclosure provides a method of treating wet macular degeneration (WMD), such as by preventing or inhibiting the formation of new blood vessels under the macula, which typically occurs during the course of this disease. In some embodiments, a subject diagnosed with WMD is administered a therapeutically effective amount of an activator of CXCR3, such as an IP-10 protein (such as the IP-10 protein of SEQ ID NO: 1) or a biologically active fragment of IP-10 (such as the IP-10 peptide of SEQ ID NO: 2, SEQ ID NO: 5, SEQ ID NO: 6, SEQ ID NO: 8 or SEQ ID NO: 9). In other embodiments, a subject diagnosed with WMD is administered a therapeutically effective amount of a PF4 protein (such as the PF4 protein of SEQ ID NO: 3) or a biologically active fragment of PF4 (such as the PF4 peptide of SEQ ID NO: 4, SEQ ID NO: 10 or SEQ ID NO: 11). The activator of CXCR3 can be administered by any suitable route, such as by injection into the vitreous humor.

C. Diabetic Retinopathy

Diabetic retinopathy refers to damage to the retina that occurs as a complication of diabetes. Diabetic retinopathy is caused by changes in the blood vessels of the retina. There are four stages: 1) mild nonproliferative retinopathy, which includes occurrence of microaneurysms; 2) moderate nonproliferative retinopathy, which includes blockage of some vessels that feed the retina; 3) severe nonproliferative retinopathy, which includes more severe vessel blockage; and 4) proliferative retinopathy, which includes growth of abnormal blood vessels on the retina and the vitreous. Damage to the retina and/or vision loss occurs when these vessel leak or hemorrhage. Macular edema may also occur, particularly during the nonproliferative stages of the condition.

The present disclosure provides a method of treating diabetic retinopathy, such as by preventing or inhibiting the formation of new blood vessels on the retina and the vitreous, which typically occurs during the course of this disease. In some embodiments, a subject diagnosed with diabetic retinopathy is administered a therapeutically effective amount of an activator of CXCR3, such as an IP-10 protein (such as the IP-10 protein of SEQ ID NO: 1), a PF4 protein (such as the PF4 protein of SEQ ID NO: 3), or a biologically active fragment of IP-10 (such as the IP-10 peptide of SEQ ID NO: 2, SEQ ID NO: 5, SEQ ID NO: 6, SEQ ID NO: 8 or SEQ ID NO: 9), or biologically active fragment of PF4 (such as the PF4 peptide of SEQ ID NO: 4, SEQ ID NO: 10 or SEQ ID NO: 11).

The following examples are provided to illustrate certain particular features and/or embodiments. These examples should not be construed to limit the disclosure to the particular features or embodiments described.

EXAMPLES

Example 1

Use of a CXCR3 Activator for the Treatment of Restenosis Following Glaucoma Treatment To test the effect of the 21 amino acid IP-10 peptide (SEQ ID NO: 2) on restenosis following glaucoma treatment, an experiment is conducted in rabbits with experimental glaucoma.

Rabbits are treated with IP-10 peptide (SEQ ID NO: 2), PF4, or a scrambled control peptide. Rabbits are treated for glaucoma by drilling an anastomy. The peptides are then injected into the aqueous humor.

Changes in pressure are evaluated before and after treatment with the peptides. It is believed that treatment with the IP-10 peptide and PF4 will prevent an increase in pressure.

Example 2

Use of a CXCR3 Activator for the Treatment of Wet Macular Degeneration

To test the effect of the 21 amino acid IP-10 peptide (SEQ ID NO: 2) on wet macular degeneration (WMD), an experiment is conducted in rabbits with experimental WMD.

Rabbits are treated with IP-10 peptide (SEQ ID NO: 2), PF4, or a scrambled control peptide by injection into the vitreous humor. Rabbits are evaluated visually over time to evaluate the effect of each peptide. Injections are repeated as necessary. It is believed that administration of IP-10 peptide or PF4 will inhibit the development of WMD and/or lead to a reversion of WMD.

Example 3

Use of CXCR3 Activators in a Surgical Model of Trabeculectomy in the Treatment of Glaucoma This example describes administration of CXCR3 activators, such as IL-10 peptide or PF4 peptide, to modulate wound healing in a rabbit model of trabeculectomy for the treatment of glaucoma.

Experimental Overview

Glaucoma is a leading cause of blindness worldwide; it affects over 2 million Americans. Damage to the optic nerve caused by glaucoma can be slowed or stopped completely by reducing the intraocular pressure (IOP) over years or decades in afflicted patients. IOP reduction is typically accomplished through either the administration of eye drops several times daily, the difficult and frequent nature of which contributes to patient compliance rates estimated to be as low as 50%, or surgically by constructing an alternate pathway for aqueous drainage from the anterior chamber of the eye. Unfortunately, glaucoma fistulizing surgery, typically by trabeculectomy or tube shunt implantation, can have high rates of failure when accompanied by exuberant tissue healing. Trabeculectomy surgery is typically modified in humans with the addition of antifibrotic agents (typically mitomycin-C or 5-fluorouracil) applied to the subconjunctival space at the time of surgery, and occasionally with subsequent injections of these agents into the subconjunctival space during the post-operative healing phase. These agents have improved the success rate of trabeculectomy in humans, but have also increased the incidence of wound breakdown, leakage, and occasional infection of the filtering bleb (blebitis) and eye (endophthalmitis). Therefore, the trabeculectomy as currently performed remains an imperfect surgery, with clinicians and investigators worldwide interested in improving the success rate while minimizing complication rates. Prior investigations have focused on the use of perioperative corticosteroids as well as anti-VEGF agents with mixed success.

The CXCR3 receptor pathway appears to signal a "stop healing" response; stimulation of the pathway in vitro has shown delayed angiogenesis and knockout murine models in vivo have shown excessive hypertrophic and hypercellular healing response. The present study investigates the use of receptor-binding ligands to modulate wound healing in a surgical model of trabeculectomy in vivo.

The goal of the present study is to evaluate the efficacy and surgical wound healing of two binding ligands of CXCR3. IP-10 is a chemokine of the CXC subfamily and ligand for the receptor CXCR3. Binding of this protein to CXCR3 results in pleiotropic effects, including stimulation of monocytes, natural killer and T-cell migration, modulation of adhesion molecule expression, and inhibition of vessel formation. IP-10 peptide (IP-10p) is a 21 amino acid fragment of IP-10 (SEQ ID NO: 2) that mimics the actions of the entire peptide on endothelial cells. Other IP-10 peptide fragments and variants include those set forth herein as SEQ ID NO: 5 (22 amino acid fragment of human IP-10), SEQ ID NO: 6 (21 amino acid peptide variant of human IP-10), SEQ ID NO: 8 (21 amino acid fragment of mouse IP-10) or SEQ ID NO: 9 (22 amino acid fragment of mouse IP-10). PF4 is a 70-amino acid protein that is released from the alpha-granules of activated platelets and binds with high affinity to heparin. Its major physiologic role appears to be neutralization of heparin-like molecules on the endothelial surface of blood vessels, thereby inhibiting local antithrombin III activity and promoting coagulation. PF4 peptide (PF4p) is a 29 amino acid fragment (SEQ ID NO: 4) of PF4, a small cytokine belonging to the CXC chemokine family. Other PF4 fragments includes those set forth herein as SEQ ID NO: 10 (13 amino acid fragment of human PF4) and SEQ ID NO: 11 (18 amino acid fragment of human PF4).

This study uses a rabbit model of trabeculectomy. A small number of rabbits (N=12) are randomized to receive one of two different binding ligands of CXCR3 at the time of trabeculectomy, and by post-operative subconjunctival injection on alternate days for the following week. Rabbit eyes are examined and photographed daily during the first two weeks, then weekly in order to document the effect of test agent on the formation and maintenance of the filtering bleb. At the end of the examination period (6 weeks), animals are euthanized and ocular tissue is sent for ocular pathology evaluation.

Experimental Procedure

1. Modified Trabeculectomy

Each rabbit is anesthetized with an intramuscular (IM) injection of ketamine (40 mg/kg) and xylazine (4 mg/kg). The animal is transferred to a procedure room and placed on a portable operating table under an operating microscope. Two drops of topical anesthetic (0.5% proparacaine) are instilled into each eye and the animal is given ketoprofen 1.5 mg/kg IM injection for post-operative pain control. The right eye is proptosed, evaluated for any pre-existing ocular defects and Betadine™ ophthalmic is administered in the eye and on the eyelid margins.

A 30-gauge needle is then used to introduce the test agent (100 μg IP-10p or 10 μg PF-10p) mixed with lidocaine (0.5 ml total volume) into the subconjunctival space in the superior quadrant of the left eye. A fornix-based conjunctival dissection is completed and a 23-gauge needle is used to create a scleral tunnel 1 mm posterior to the limbus for insertion of a 22-gauge cannula (Insyte(r); Becton Dickinson Vascular Access, Sandy, Utah) into the anterior chamber. The cannula is inserted such that the distal end crosses the pupillary margin to avoid tube-iris capture. The tube is then secured to the scleral bed with 10-0 nylon suture (Ethicon Inc., Somerville, N.J.) and efflux of fluid into the subconjunctival space is confirmed. The left eye of each animal (in both treatment agent groups) undergoes the exact procedure as noted above except that lidocaine without test agent (0.5 ml total volume) is injected subconjunctivally. In all eyes, 50 mg (0.25 ml of 200 mg/ml) ceftazidime and 2.5 mg (0.25 ml of 10 mg/ml) dexamethasone is injected into the subconjunctival space at the end of surgery. This provides immediate control of post-operative inflammation and infection prophylaxis.

2. Slit-Lamp Examination and Photography

Rabbits are examined and photographed daily for 2 weeks after the modified trabeculectomy. Animals are given topical anesthetic (proparacaine) at the start of each exam. There should be no pain involved in the examination and photography, as this is routinely performed painlessly in humans. After topical drops (including anesthesia) are administered, IOP is checked using a tonometer. This takes less than 20 seconds and is painless when done right after topical anesthesia. Slit lamp exam is either with a hand-held portable slit lamp or with standard upright slit lamp. The animals require restraint for both of these, however it is brief and each exam and photograph is accomplished within 3-4 minutes. Restraint for hand-held slit lamp and photography is accomplished by gently holding the rabbit's head and upper body to immobilize them while the left eye is held open for a brief look and photo. For upright slit lamp, rabbits are placed in the Romanowski II rabbit holder that comfortably restrains the rabbits by wrapping Velcro™ straps around it holding it securely to a stand with all 4 limbs hanging over the sides. Eyes are opened and examined non-invasively. Photographs are taken using the camera on the slit lamp. Rabbits are acclimated to the Romanowski II rabbit holder on the day prior to modified trabeculectomy. During this time, the eyes are examined for any pre-existing ocular defects using the slit-lamp. They are in the holder for no more than 3-4 minutes for any examination.

3. Subconjunctival Injection of Test Agents

On post-operative days 2, 4, and 7, subconjunctival injection of the test agent is performed in the area of the trabeculectomy surgery in the right eyes, at the dosage described above mixed with lidocaine. Subconjunctival injection of lidocaine without test agent is performed for the left eyes. This requires repeat sedation as described above. This can be performed in conjunction with that day's slit lamp exam and photography.

4. Euthanasia

After the examination period of 6 weeks total, the rabbits are euthanized with an intravenous (IV) injection (ear vein) of Euthasol™ Solution following systemic anesthesia with an IM injection of a combination of ketamine (33 mg/kg) and xylazine (3 mg/kg). Each eye is removed and sent for pathologic evaluation of the involved tissues.

Results

It is expected that this treatment method will demonstrate an effective, sustained treatment of elevated IOP with improved bleb morphology and fewer surgical complications.

In view of the many possible embodiments to which the principles of the disclosed invention may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

The invention claimed is:

1. A method of treating an angiogenic disorder of the eye, or treating aberrant angiogenesis of the eye in a subject in need thereof, comprising administering to the subject a therapeutically effective amount of an activator of C-X-C chemokine receptor 3 (CXCR3), wherein the CXCR3 activator is a biologically active interferon-γ-inducible 10 kDa protein (IP-10) peptide fragment that is no more than 40 amino acids in length and comprises the amino acid sequence of SEQ ID NO: 2, thereby treating the angiogenic disorder, or treating the aberrant angiogenesis.

2. The method of claim 1, wherein the angiogenic disorder of the eye is an intraocular angiogenic disorder.

3. The method of claim 2, wherein the intraocular angiogenic disorder is selected from the group consisting of restenosis following glaucoma treatment, wet macular degeneration, diabetic retinopathy, retinopathy of prematurity and neovascular glaucoma.

4. The method of claim 1, wherein the angiogenic disorder of the eye is an external angiogenic disorder of the eye.

5. The method of claim 4, wherein the external angiogenic disorder of the eye is corneal neovascularization.

6. The method of claim 1, wherein the aberrant angiogenesis is caused by restenosis following glaucoma treatment, wet macular degeneration, diabetic retinopathy, retinopathy of prematurity, neovascular glaucoma or corneal neovascularization.

7. The method of claim 1, wherein the peptide is conjugated to polyethylene glycol (PEG) or dextran.

8. The method of claim 1, wherein the peptide is administered topically, by injection or by medical implant.

9. The method of claim 8, wherein the peptide is administered topically in a cream or eye drop.

10. The method of claim 8, wherein the peptide is administered by injection into the vitreous humor or the aqueous humor.

11. The method of claim 8, wherein the peptide is impregnated in the medical implant, is coated on the surface of the medical implant, or both.

12. The method of claim 1, wherein the peptide is present in a pharmaceutically acceptable carrier acceptable for administration to the eye.

13. The method of claim 1, wherein the IP-10 peptide consists of SEQ ID NO: 2.

14. A method of treating an angiogenic disorder of the eye, or treating aberrant angiogenesis of the eye in a subject in need thereof, comprising administering to the subject a therapeutically effective amount of an activator of C-X-C chemokine receptor 3 (CXCR3), wherein the CXCR3 activator is a biologically active interferon-γ-inducible 10 kDa protein (IP-10) peptide fragment that is no more than 40 amino acids in length and comprises the amino acid sequence of SEQ ID NO: 5, thereby treating the angiogenic disorder, or treating the aberrant angiogenesis.

15. The method of claim 14, wherein the angiogenic disorder of the eye is an intraocular angiogenic disorder.

16. The method of claim 15, wherein the intraocular angiogenic disorder is selected from the group consisting of restenosis following glaucoma treatment, wet macular degeneration, diabetic retinopathy, retinopathy of prematurity and neovascular glaucoma.

17. The method of claim 14, wherein the angiogenic disorder of the eye is an external angiogenic disorder of the eye.

18. The method of claim 17, wherein the external angiogenic disorder of the eye is corneal neovascularization.

19. The method of claim 14, wherein the aberrant angiogenesis is caused by restenosis following glaucoma treatment, wet macular degeneration, diabetic retinopathy, retinopathy of prematurity, neovascular glaucoma or corneal neovascularization.

20. The method of claim 14, wherein the peptide is conjugated to polyethylene glycol (PEG) or dextran.

21. The method of claim 14, wherein the peptide is administered topically, by injection or by medical implant.

22. The method of claim 21, wherein the peptide is administered topically in a cream or eye drop.

23. The method of claim 21, wherein the peptide is administered by injection into the vitreous humor or the aqueous humor.

24. The method of claim 21, wherein the peptide is impregnated in the medical implant, is coated on the surface of the medical implant, or both.

25. The method of claim 14, wherein the peptide is present in a pharmaceutically acceptable carrier acceptable for administration to the eye.

26. The method of claim 14, wherein the IP-10 peptide consists of SEQ ID NO: 5.

* * * * *